(12) United States Patent
Kim

(10) Patent No.: US 11,464,898 B2
(45) Date of Patent: Oct. 11, 2022

(54) FLUSHING APPARATUS FOR INJECTION OF HAZARDOUS MEDICINAL LIQUID, AND HAZARDOUS MEDICINAL LIQUID INJECTION APPARATUS

(71) Applicant: Yong Hyun Kim, Gyeonggi-do (KR)

(72) Inventor: Yong Hyun Kim, Gyeonggi-do (KR)

( * ) Notice: Subject to any disclaimer, the term of this patent is extended or adjusted under 35 U.S.C. 154(b) by 275 days.

(21) Appl. No.: 16/757,114

(22) PCT Filed: Sep. 7, 2018

(86) PCT No.: PCT/KR2018/010470
§ 371 (c)(1),
(2) Date: Apr. 17, 2020

(87) PCT Pub. No.: WO2019/078487
PCT Pub. Date: Apr. 25, 2019

(65) Prior Publication Data
US 2020/0338260 A1    Oct. 29, 2020

(30) Foreign Application Priority Data

Oct. 20, 2017  (KR) .................... 10-2017-0136432
Mar. 6, 2018   (KR) .................... 10-2018-0026509

(51) Int. Cl.
*A61M 5/14*     (2006.01)
*A61M 39/10*    (2006.01)
*A61M 39/24*    (2006.01)

(52) U.S. Cl.
CPC .......... *A61M 5/14* (2013.01); *A61M 39/1055* (2013.01); *A61M 39/24* (2013.01);
(Continued)

(58) Field of Classification Search
CPC .............. A61M 39/223; A61M 39/225; A61M 2039/0018; A61M 2039/2039; A61M 2039/2493
See application file for complete search history.

(56) References Cited

U.S. PATENT DOCUMENTS 4,173,222 A     11/1979  Muetterties
4,337,770 A  *  7/1982   Young ................. A61B 5/0215
                                              604/93.01
(Continued)

FOREIGN PATENT DOCUMENTS

KR         20-0201601 Y1   11/2000
KR      10-2005-0085207 A   6/2007
(Continued)

OTHER PUBLICATIONS

Extended European Search Report dated Sep. 30, 2020.

*Primary Examiner* — Manuel A Mendez
*Assistant Examiner* — Courtney B Fredrickson
(74) *Attorney, Agent, or Firm* — Clark Hill PLC; James R. Foley

(57) ABSTRACT

A flushing apparatus according to embodiments of the present disclosure includes: a main body configured to connect a connection pipe for guiding a hazardous medicinal liquid harmful to a human body when exposed to an ambient air and a patient connection module for injecting the hazardous medicinal liquid into a patient, the main body configured to form a first flow path for guiding the hazardous medicinal liquid from the connection pipe to the patient connection module, the main body including a flushing portion forming a second flow path connected to a predetermined connection point located between both ends of the first flow path; and a flow rate reduction part disposed at upstream side of the connection point in the first flow path and configured to reduce a flow rate of the hazardous medicinal liquid flowing through the first flow path. The present disclosure shows various embodiments of the flushing apparatus.

11 Claims, 10 Drawing Sheets

(52) U.S. Cl.
CPC ............... *A61M 2005/1403* (2013.01); *A61M 2202/049* (2013.01); *A61M 2205/3334* (2013.01)

(56) References Cited

U.S. PATENT DOCUMENTS

| | | |
|---|---|---|
| 4,919,167 A | 4/1990 | Manska |
| 5,011,477 A | 4/1991 | Winchell et al. |
| 5,700,257 A * | 12/1997 | Minick ............. A61M 5/14244 604/408 |
| 2003/0217976 A1 * | 11/2003 | Bowman, Jr. ......... A61M 1/288 210/741 |
| 2008/0166292 A1 | 7/2008 | Levin et al. |
| 2008/0287906 A1 | 11/2008 | Burkholz |
| 2009/0306621 A1 | 12/2009 | Thome, Jr. et al. |
| 2011/0276010 A1 | 11/2011 | Davis |
| 2011/0276031 A1 | 11/2011 | Hoang et al. |
| 2017/0241583 A1 | 8/2017 | Schinazi |

FOREIGN PATENT DOCUMENTS

| | | | |
|---|---|---|---|
| KR | 10-1424934 B1 | 8/2014 | |
| KR | 10-2016-0029411 A | 8/2016 | |
| WO | WO-9515194 A1 * | 6/1995 | .......... A61M 39/045 |
| WO | 2014/132293 A1 | 9/2014 | |
| WO | 2015/037928 A1 | 3/2015 | |

* cited by examiner

FLUSHING APPARATUS FOR INJECTION OF HAZARDOUS MEDICINAL LIQUID, AND HAZARDOUS MEDICINAL LIQUID INJECTION APPARATUS

TECHNICAL FIELD

The present disclosure relates to a medical apparatus for injecting a hazardous medicinal liquid.

BACKGROUND

In order to supply a medicine to a patient, a medicinal liquid injection apparatus for injecting a liquid medicine into a patient is known. By using the medicinal liquid injection apparatus, a medicinal liquid stored in a predetermined storage space is introduced into the body of a patient through a passage (e.g., an inner space of a tube and an injection needle) connected to the patient.

Meanwhile, hazardous medicines that have a harmful effect on the human body when exposed to the ambient air are known. For example, as such a hazardous medicine, an anti-cancer agent such as 5-FU or the like can be mentioned. When injecting a "liquid hazardous medicine" (hereinafter referred to as "hazardous medicinal liquid") into a patient using the medicinal liquid injection apparatus, if the hazardous medicinal liquid is exposed to the ambient air around the medicinal liquid injection apparatus, the hazardous medicinal liquid may be coated on the skin of a human body or may be vaporized and introduced into the respiratory tract of a human body, thereby causing fatal harm to the patient and medical staff (doctors, nurses, etc.).

For medical purposes, there is known a flow rate control module configured to prevent a hazardous medicinal liquid from being injected into a patient's body at once and to slowly inject the hazardous medicinal liquid into the patient's body over a considerable period of time. The flow rate control module is disposed in the passage of the medicinal liquid injection apparatus to reduce the flow rate of a liquid flowing in the passage.

Meanwhile, in order to prevent the air from flowing into the body of a patient in the process of using the medicinal liquid injection apparatus, there is known a priming operation for filling a liquid (e.g., a medicinal liquid to be injected) in a passage (e.g., an inner space of a tube and an injection needle) to be connected to the patient, before the injection needle is connected to the patient.

If the passage is filled with the hazardous medicinal liquid during the priming operation before injecting the hazardous medicinal liquid into a patient, there is a risk that the hazardous medicinal liquid is exposed to the ambient air at the tip of an injection needle. Accordingly, in the prior art, there is known a method of filling the passage with a priming liquid, which is harmless to the human body, during the priming operation before injecting the hazardous medicinal liquid.

In a conventional medicinal liquid injection apparatus, a predetermined inlet port for introducing the priming liquid into the passage is formed. In order to fill the entire interior of the passage with the priming liquid during the priming operation, the inlet port is disposed at an upstream side of the passage. Accordingly, in the conventional medicinal liquid injection apparatus, the flow rate reduction module is disposed at downstream side of the inlet port.

SUMMARY

The present disclosure may help medical staff to safely and conveniently perform medical activities using a hazardous medicine.

In the prior art, there is still a problem that when the injection needle is separated from a patient after the injection of the hazardous medicine into the patient is completed, the hazardous medicine may be discharged from the tip of the injection needle, which may cause fatal harm to the human body. The present disclosure may help to easily perform a flushing process, which will be described below, to solve such a problem.

In the prior art, there is a problem that when a flushing liquid to be described later is introduced into a passage through the inlet port for the introduction of the priming liquid to perform the flushing process, the time required for the flushing process is lengthened due to the flow rate reduction module disposed at a downstream side of the inlet port. In particular, when the injection of the hazardous medicinal liquid is stopped in the middle of the injection of the hazardous medicinal liquid and the flushing process is performed according to a sudden medical necessity such as a side effect of injecting a hazardous medicinal liquid, if the flushing liquid is introduced through the inlet port, there is a problem that a large delay in a medical action may occur, thereby causing irreparable damage to a patient. A problem is also posed that a considerable amount of hazardous medicinal liquid remaining on the downstream side of the inlet port in the passage may be unnecessarily injected into the patient. The present disclosure may solve such a problem, thereby helping to complete the flushing process as soon as possible after the flushing process has begun, and reducing the amount of hazardous medicinal liquid that is unnecessarily and additionally injected into a patient.

The present disclosure may help to solve the above problems and to perform the priming operation safely and conveniently.

After the hazardous medicinal liquid is injected into a patient, the hazardous medicinal liquid remains inside the medicinal liquid injection apparatus. In the related art, there is a risk that the hazardous medicinal liquid remaining inside the medicinal liquid injection apparatus is leaked to the outside during disposal of the medicinal liquid injection apparatus which has been used for injecting the hazardous medicinal liquid. The present disclosure may reduce the risk of leakage of the hazardous medicinal liquid from the used medicinal liquid injection apparatus.

A flushing apparatus for injection of a hazardous medicinal liquid according to one embodiment of the present disclosure may include: a main body configured to connect a connection pipe for guiding a hazardous medicinal liquid harmful to a human body when exposed to an ambient air and a patient connection module for injecting the hazardous medicinal liquid into a patient, the main body configured to form a first flow path for guiding the hazardous medicinal liquid from the connection pipe to the patient connection module, the main body including a flushing portion forming a second flow path connected to a predetermined connection point located between both ends of the first flow path; and a flow rate reduction part disposed at upstream side of the connection point in the first flow path and configured to reduce a flow rate of the hazardous medicinal liquid flowing through the first flow path.

A hazardous medicinal liquid injection apparatus according to one embodiment of the present disclosure may include: a pumping module configured to pressurize a hazardous medicinal liquid; a connection pipe configured such that the hazardous medicinal liquid flowing out of the pumping module by the pressurization in the pumping module flows through the connection pipe; and the flushing apparatus.

In some embodiments, the main body may include an integrally-formed joint part. The joint part may form a connection flow path, which is a portion of the first flow path, extending from a downstream end of the flow rate reduction part to the connection point.

By the flushing apparatus, it is possible to help medical staff and a patient to safely handle the hazardous medicinal liquid and to improve the convenience of the medical activity of injecting the hazardous medicinal liquid performed by medical staff.

In addition, by the flushing apparatus, while conveniently using the function of the flow rate reduction part, it is possible to shorten the time required for the flushing operation and to reduce the amount of hazardous medicinal liquid unnecessarily injected to a patient under the situation of urgently separating the patient connection module from the patient.

In addition, by providing the joint part, it is possible to reduce the probability of occurrence of a dangerous situation in which when disposing the flushing apparatus after the flushing operation, the joint part is separated and the hazardous medicinal liquid existing inside the flushing apparatus is exposed to the outside.

In addition, since the joint part does not require a separation and assembly process, it is possible to significantly reduce the probability of introduction of an unsanitary foreign substance or an infectious material such as a virus or the like into the flow path.

BRIEF DESCRIPTION OF THE DRAWINGS

In FIG. 3, there is illustrated a partially enlarged view showing a partial actuation mechanism.

DETAILED DESCRIPTION

Figure 1A:
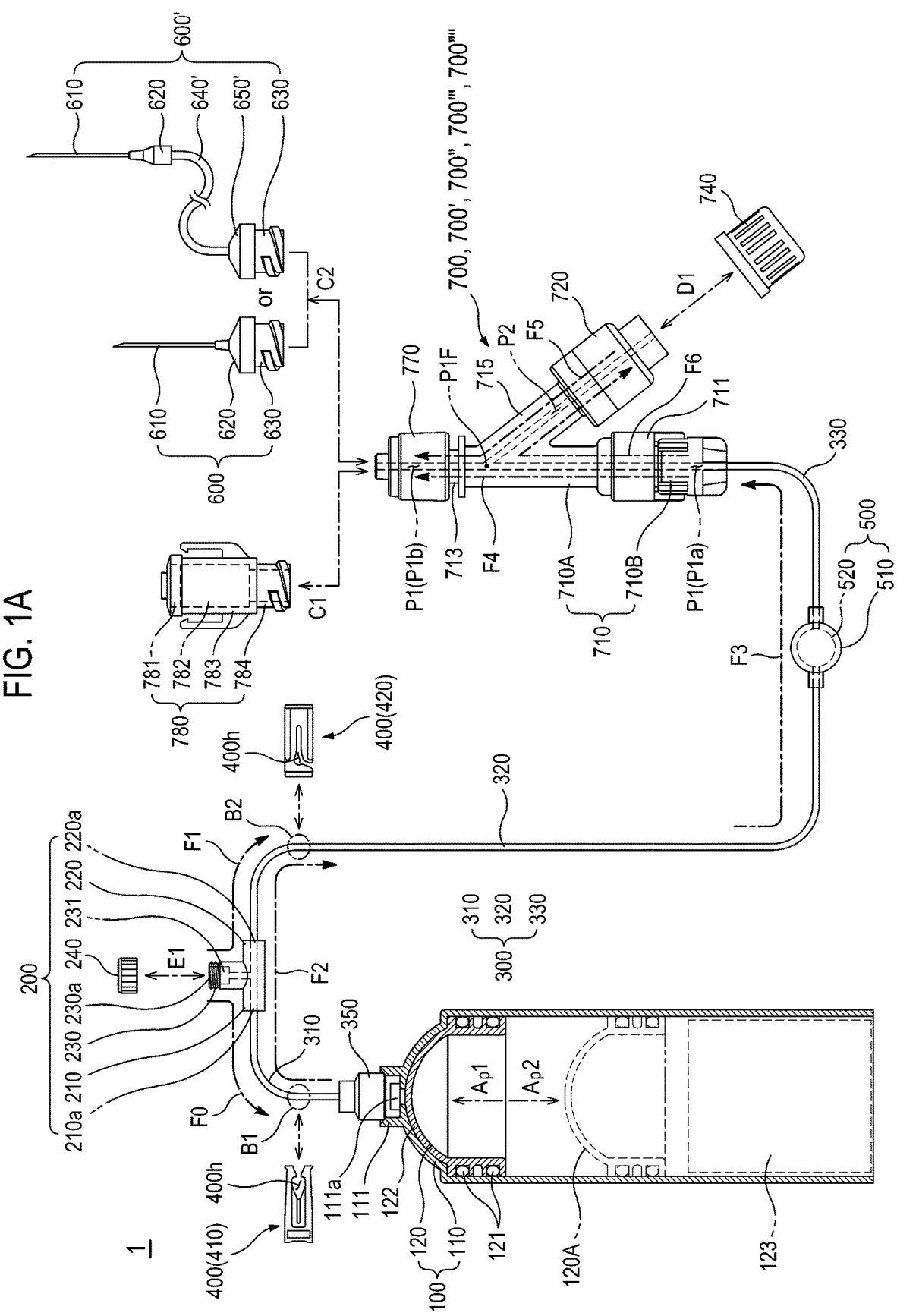
FIG. 1A is a conceptual diagram illustrating an entire system of a hazardous medicinal liquid injection apparatus 1 according to one embodiment of the present disclosure.

Embodiments of the present disclosure are illustrated for the purpose of explaining the technical idea of the present disclosure. The scope of the rights according to the present disclosure is not limited to the embodiments presented below or the detailed descriptions of such embodiments.

All technical and scientific terms used in the present disclosure have a meaning generally understood by those of ordinary skill in the art to which the present disclosure pertains, unless otherwise defined. All terms used in the present disclosure are chosen for the purpose of more clearly describing the present disclosure and are not chosen to limit the scope of rights according to the present disclosure.

As used in the present disclosure, expressions such as "comprising", "including", "having", and the like are to be understood as open-ended terms having the possibility of encompassing other embodiments, unless otherwise mentioned in the phrase or sentence containing such expressions.

The singular form described in the present disclosure may include a plural meaning, unless otherwise mentioned. This applies equally to the singular form recited in the claims.

The terms "first", "second", etc. used in the present disclosure are used to distinguish a plurality of components from one another, and do not limit the order, importance or master-servant relationship of the relevant components.

Hereinafter, descriptions are made as to embodiments of the present disclosure with reference to the accompanying drawings. In the accompanying drawings, in order to distinguish different embodiments, a prime symbol ' or multi-prime symbols ", ''' and '''' may be indicated after the reference numeral. In the accompanying drawings, the same or corresponding elements are denoted by the same reference numerals. In the following descriptions of the embodiments, descriptions of the same or corresponding elements may be omitted. However, even if the descriptions of elements are omitted, it is not intended that such elements are not included in a certain embodiment.

As used herein, the term "hazardous medicinal liquid" means a medicinal liquid which is harmful to a human body when exposed to an ambient air. The hazardous medicinal liquid is a medicinal liquid which is known to adversely affect a human body when coated on the skin of the human body or when vaporized and introduced into the respiratory tract of the human body. For example, the hazardous medicinal liquid may include a solution of anti-cancer agent such as 5-FU or the like.

Hereinafter, the hazardous medicinal liquid injection apparatuses 1 and 1' according to one embodiment and another embodiment of the present disclosure will be described with reference to FIGS. 1A and 1B. The hazardous medicinal liquid injection apparatus 1 or 1' includes a pumping module 100 configured to pressurize a hazardous medicinal liquid. The hazardous medicinal liquid injection apparatus 1 or 1' includes a connection pipe 300 or 300' for guiding the hazardous medicinal liquid. The hazardous medicinal liquid flowing out of the pumping module 100 by the pressurization in the pumping module 100 flows through the connection pipe 300 or 300'.

The hazardous medicinal liquid injection apparatus 1 or 1' may include a port module 200 or 200' connected to the connection pipe 300 or 300' or the pumping module 100. The port module 200 or 200' is configured to be able to fill a liquid (e.g., a hazardous medicinal liquid or a priming liquid) into the pumping module 100. A liquid introduced through the port module 200 or 200' may flow into the pumping module 100.

The priming liquid refers to a liquid which is harmless to a human body even when exposed to an ambient air and which does not cause a problem even when introduced into the human body. For example, a saline solution may be used as the priming liquid.

The hazardous medicinal liquid injection apparatus 1 or 1' may include a connection pipe opening/closing module 400 or 400' configured to switch opening and closing of at least one point of the connection pipe 300 or 300'. The hazardous medicinal liquid injection apparatus 1 or 1' may include a filter module 500 for filtering out foreign substances from a liquid flowing through the connection pipe 300 or 300'.

The hazardous medicinal liquid injection apparatus 1 or 1' may include a patient connection module 600 or 600' for injecting the hazardous medicinal liquid into a patient. The patient connection module 600 or 600' may include a component to be inserted into the body of a patient, such as an injection needle 610 or the like.

The patient connection module 600 or 600' may include an inserting component including an element configured to be inserted into the body of a patient, such as an injection needle 610 or the like and a remaining component. The inserting component and the remaining component may be detachably coupled to each other. In this case, in a state in which the inserting component is connected to the patient and detached from the remaining component, the user may couple the remaining component to the flushing apparatus 700, 700', 700", 700''' or 700'''' and then couple the inserting component and the remaining component to each other. In this case, a liquid that has passed through the flushing apparatus 700, 700', 700", 700''' or 700'''' may flow into the body of the patient after sequentially passing through the remaining component and the inserting component.

The hazardous medicinal liquid injection apparatus 1 or 1' includes a flushing apparatus 700, 700', 700", 700''' or 700'''' configured to connect the connection pipe 300 or 300' and the patient connection module 600 or 600'. The flushing apparatus 700, 700', 700", 700''' or 700'''' forms a first flow path P1 configured to guide the hazardous medicinal liquid from the connection pipe 300 or 300' to the patient connection module 600 or 600'. The flushing apparatus 700, 700', 700", 700''' or 700'''' forms a second flow path P2 connected to a predetermined connection point P1F located between both ends of the first flow path P1. A flushing liquid may be introduced into the first flow path P1 from the outside through the second flow path P2.

The flushing liquid refers to a liquid which is harmless to a human body even when exposed to an ambient air and which does not cause a problem even when introduced into the human body. For example, a saline solution may be used as the flushing liquid.

A process of injecting the hazardous medicinal liquid into a patient using the hazardous medicinal liquid injection apparatus 1 or 1' according to the embodiments of the present disclosure may include a priming process, a medicinal liquid injecting process and a flushing process, which are performed sequentially.

The priming process is performed in a state in which the patient connection module 600 or 600' is separated from a patient, or in a state in which the inserting component of the patient connection module 600 or 600' is connected to a patient with the remaining component separated. In the priming process, the priming liquid is filled in a predetermined passage configured such that the hazardous medicinal liquid flows through the predetermined passage. After performing the priming process, by connecting the patient connection module 600 or 600' to the patient or by coupling the inserting component to the remaining component, it is possible to prevent the hazardous medicinal liquid from being exposed to the ambient air in the priming process.

In the present embodiment, the predetermined passage includes the connection pipe 300 or 300' and the flushing apparatus 700, 700', 700", 700''' or 700''''. The predetermined passage may further include the patient connection module 600 or 600' connected to the flushing apparatus 700, 700', 700", 700''' or 700''''.

After connecting the patient connection module 600 or 600' to a patient, the medicinal liquid injecting process is performed. In the medicinal liquid injecting process, the hazardous medicinal liquid flows along the predetermined passage by the pressurization in the pumping module 100. Accordingly, at the beginning of the medicinal liquid injecting process, the priming liquid filled in the predetermined passage is introduced into the body of a patient. Thereafter, the hazardous medicinal liquid flowing behind the priming liquid begins to flow into the body of a patient.

After the medicinal liquid injecting process, the flushing process is performed. In the flushing process, the flushing liquid is introduced into a predetermined intermediate point in the predetermined passage through the flushing apparatus 700, 700', 700", 700''' or 700''''. In the flushing process, the introduced flushing liquid pushes the hazardous medicinal liquid filled in the downstream portion of the predetermined passage in a downstream direction. Accordingly, at the beginning of the flushing process, the hazardous medicinal liquid filled in the downstream portion of the predetermined passage is introduced into the body of the patient. Thereafter, the flushing liquid flowing behind the hazardous medicinal liquid begins to flow into the body of the patient. After the flushing liquid begins to flow into the body of the patient, the flushing process may be terminated by disconnecting the patient connection module 600 or 600' from the patient, and it is possible to finish the process of injecting the hazardous medicinal liquid without exposing the hazardous medicinal liquid to the ambient air.

As used herein, the terms "upstream" and "downstream" are defined based on the direction in which the hazardous medicinal liquid flows in the connection pipe 300 or 300', a flow path P and the patient connection module 600 or 600' when the pumping module 100 pressurizes the hazardous medicinal liquid. Specifically, the directions of arrows F2, F3 and F4 in FIGS. 1A and 1B are defined as a downstream direction, and the opposite direction of the downstream direction is defined as an upstream direction.

Referring to 1A and 1, the pumping module 100 includes a chamber 110 configured to accommodate the hazardous medicinal liquid. The chamber 110 forms an internal space together with a pressurization unit 120. The hazardous medicinal liquid may be stored in the internal space. In another embodiment, the priming liquid may be temporarily stored in the internal space.

In the chamber 110, a discharge port portion 111, through which a liquid in the chamber 110 is discharged, is formed. The discharge port portion 111 may protrude from the outer surface of the chamber 110.

In the present embodiment, a valve 111a may be disposed in the discharge port portion 111. The valve 111a may be configured to open the discharge port portion 111 when pressed by a module connection portion 350 disposed at an upstream end of the connection pipe 300 or 300'. The valve 111a may include a swabable valve 111a. The swabable valve 111a includes a surface that forms a hole which is configured to be opened when pressed from the outside. The swabable valve 111a is configured to allow a user to wipe the surface thereof.

The pumping module 100 includes a pressurization unit 120 for pressurizing a liquid stored in the chamber 110. The pressurization unit 120 may be disposed inside the chamber 110. The pressurization unit 120 includes a pressurization surface 122 facing the internal space of the chamber 110. The pressurization surface 122 may contact the liquid in the chamber 110 to directly push the liquid. The pressurization surface 122 may pressurize the liquid in the chamber 110 by moving in a predetermined pressurization direction Ap1. When the liquid is being filled into the chamber 110, the pressurization surface 122 moves in the direction Ap2 opposite to the pressurization direction Ap1. In FIGS. 1A and 1B, the position in a state in which the pressurization surface 122 and a sliding part 121 are moved in the opposite direction Ap2 is denoted by reference numeral 120A.

The pressurization unit 120 includes the sliding part 121 configured to slidingly move along the inner surface of the chamber 110. The sliding part 121 is configured to move integrally with the pressurization surface 122. The sliding part 121 may be configured to prevent a liquid in the chamber 110 from leaking through between the pressurization surface 122 and the inner surface of the chamber 110.

The pressurization unit 120 may include a pressurization operation part 123 that provides power to move the pressurization surface 122 in the pressurization direction Ap1. As an example, the pressurization operation part 123 may be configured to pressurize a liquid in the chamber 110 by using a volume expansion due togas activation. As another example, the pressurization operation part 123 may provide a portion that can be grabbed by a user, such that the pressurization surface 122 can be moved in the pressurization direction Ap1 by the user's force.

Although not shown, in a further example, the pressurization unit 120 may be configured to pressurize a liquid using an elastic force of an elastic body such as a balloon or the like. In this case, the pressurization unit 120 may be configured to pressurize a liquid in a balloon.

The port module 200 or 200' is configured to be able to fill a liquid into the chamber 110. A liquid may be introduced into the connection pipe 300 or 300' or the chamber 110 from the outside through the port module 200 or 200'. The port module 200 or 200' is connected to the connection pipe 300 or 300' or the chamber 110.

A liquid may move into the connection pipe 300 or 300'. The upstream end of the connection pipe 300 or 300' is connected to the pumping module 100. A downstream end of the connection pipe 300 or 300' is connected to the flushing apparatus 700, 700', 700", 700''' or 700''''. The connection pipe 300 or 300' guides the movement of the hazardous medicinal liquid from the pumping module 100 to the flushing apparatus 700, 700', 700", 700''' or 700''''. The connection pipe 300 or 300' may be formed of a flexible material.

The hazardous medicinal liquid injection apparatus 1 or 1' includes a module connection portion 350 connected to the discharge port portion 111. A liquid discharged from the discharge port portion 111 through the module connection portion 350 may be introduced into the connection pipe 300 or 300'.

In the present embodiment, the module connection portion 350 may be configured to be coupled to the discharge port portion 111 by the user. The module connection portion 350 may be configured such that the module connection portion 350 cannot be separated in a general manner by the user once it is coupled to the discharge port portion 111. Specifically, in a state in which the module connection portion 350 is separated from the discharge port portion 111 at first, the discharge port portion 111 is kept in a closed state by the valve 111a. When the module connection portion 350 is coupled to the discharge port portion 111, a portion of the module connection portion 350 presses the valve 111a, thereby opening the discharge port portion 111 that has been kept in the closed state. In a state in which the discharge port portion 111 is opened, the liquid in the chamber 110 may be introduced into the connection pipe 300 or 300' through the discharge port portion 111. The module connection portion 350 may be configured such that the module connection portion 350 cannot be separated in a general manner by the user, once it is coupled to the discharge port portion 111 by the user.

Although not shown, in another example, the upstream end of the connection pipe 300 or 300' may be bonded to the discharge port portion 111 without having to perform coupling by the user. In this case, a separate valve may not be disposed in the discharge port portion 111.

At least one connection pipe opening/closing module 400 or 400' may be provided. In the present embodiment, the connection pipe opening/closing module 400 or 400' may press the outer surface of the connection pipe 300 or 300' to prevent the flow of a liquid at one point of the connection pipe 300 or 300'. The connection pipe opening/closing module 400 or 400' may have a connection pipe insertion groove 400h. A portion of the connection pipe 300 or 300' is inserted into the connection pipe insertion groove 400h, whereby the passage in the portion of the connection pipe 300 or 300' may be kept in a closed state.

The filter module 500 may be disposed in the connection pipe 300 or 300'. The filter module 500 includes a filter casing 510 connected at both ends to the connection pipe 300 or 300', respectively. The filter casing 510 forms a passage for continuously connecting flow paths formed by the connection pipe 300 or 300' connected to both ends thereof. The filter module 500 includes a filter 520 disposed in the passage of the filter casing 510.

The patient connection module 600 or 600' may be connected to the flushing apparatus 700, 700', 700", 700''' or 700''''. The patient connection module 600 or 600' may be detachably coupled to the flushing apparatus 700, 700', 700", 700''' or 700''''. A liquid that has passed through the interior of the flushing apparatus 700, 700', 700", 700''' or 700'''' may be moved to the patient connection module 600 or 600' and introduced into the body of a patient.

The patient connection module 600 or 600' may include an injection needle 610 configured to be able to invade the skin of a patient. The patient connection module 600 or 600' includes an injection support portion 620 configured to support the injection needle 610.

The patient connection module 600 or 600' includes a module coupling portion 630 coupled to a downstream portion 713 of the flushing apparatus 700, 700', 700", 700''' or 700''''. The module coupling portion 630 may be detachably coupled to a replacement coupling portion 770 of the flushing apparatus to be described later. One of the module coupling portion 630 and the replacement coupling portion 770 may be formed with a male thread and the other may be formed with a female thread that engages the male thread. An arrow C2 in FIGS. 1A and 1B indicates the coupling/detachment direction of the module coupling portion 630 with respect to the downstream portion 713.

For example, the patient connection module 600 may be configured by sequentially connecting the injection needle 610, the injection support portion 620 and the module coupling portion 630. In this case, a liquid flowing out of the downstream portion 713 of the flushing apparatus 700, 700', 700", 700''' or 700'''' may be introduced into the body of a patient after sequentially passing through the module coupling portion 630, the injection support portion 620 and the injection needle 610.

In another example, the patient connection module 600' further includes a patient connection pipe fixing portion 650' connected to the downstream side of the module coupling portion 630. The patient connection module 600' further includes a patient connection pipe 640' connecting the patient connection pipe fixing portion 650' and the injection support portion 620. The patient connection pipe 640' may be formed of a flexible material. The patient connection module 600' may be configured by sequentially connecting the injection needle 610, the injection support portion 620, the patient connection pipe 640', the patient connection pipe fixing portion 650' and the module coupling portion 630. In this case, a liquid flowing out of the downstream portion 713 of the flushing apparatus 700, 700', 700", 700''' or 700'''' may be introduced into the body of a patient after sequentially passing through the module coupling portion 630, the patient connection pipe fixing portion 650', the patient connection pipe 640', the injection support portion 620 and the injection needle 610. For example, the aforementioned inserting component is composed of the injection needle 610 and the injection support portion 620, and the aforementioned remaining component may be composed of the module coupling portion 630, the patient connection pipe fixing portion 650' and the patient connection pipe 640'.

Figure 1B:
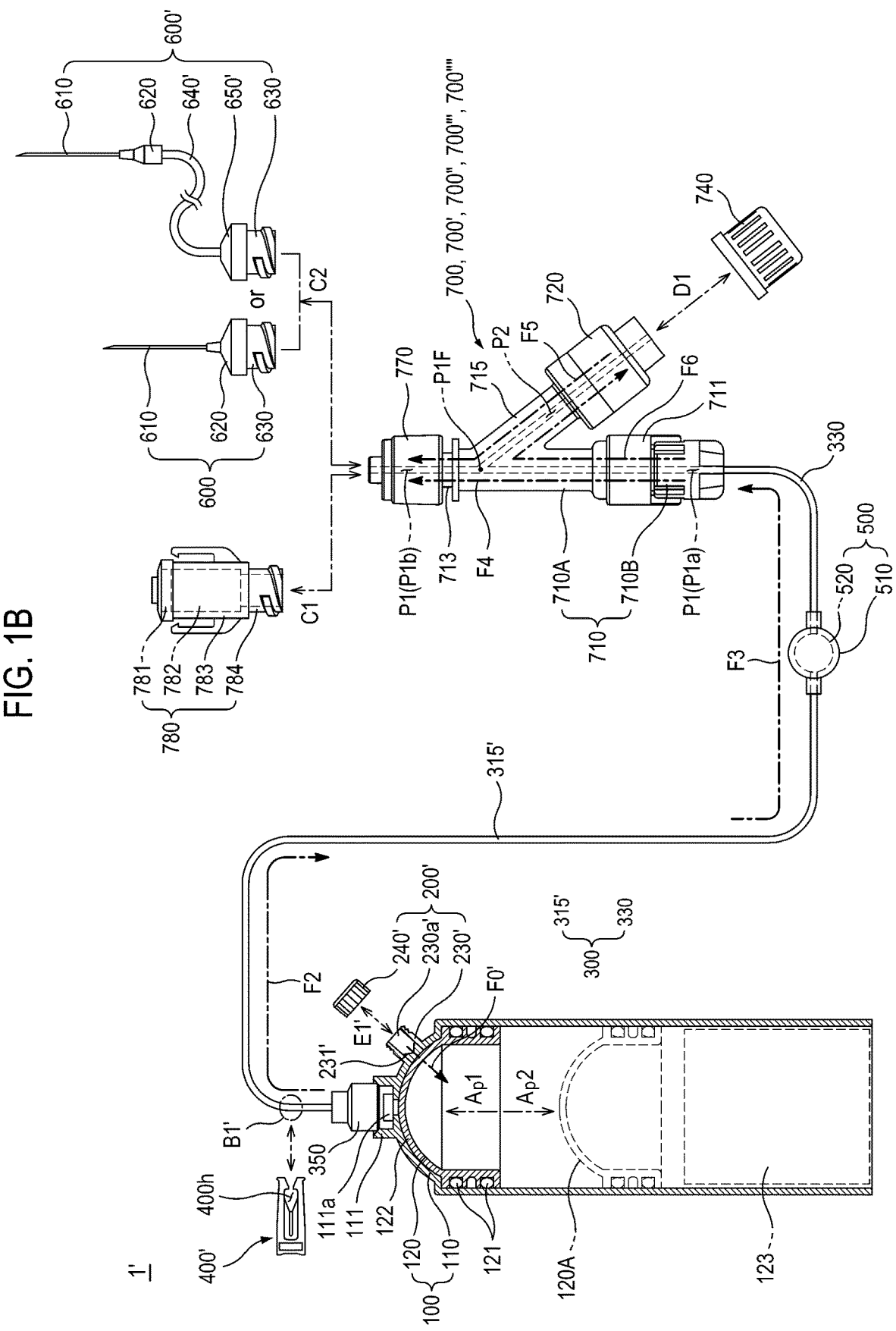
FIG. 1B is a conceptual diagram illustrating an entire system of a hazardous medicinal liquid injection apparatus 1' according to another embodiment of the present disclosure.

Referring to FIGS. 1A and 1B, the flushing apparatus 700, 700', 700", 700''' or 700'''' includes a main body 710 that forms the first flow path P1. The main body 710 forms the second flow path P2. In addition, the main body 710 includes an upstream portion 711 that forms an upstream flow path portion P1a. The main body 710 includes a downstream flow 713 that forms the downstream flow path portion P1b. The main body 710 includes a flushing portion 715 that forms the second flow path P2.

The flushing apparatus 700, 700', 700", 700''' or 700'''' includes a flushing valve unit 720 coupled to the flushing portion 715. The flushing valve unit 720 is configured to open and close the second flow path P2. In some embodiments, the flushing valve unit 720 may be detachably coupled to the flushing portion 715.

The flushing apparatus 700, 700', 700", 700''' or 700'''' includes a flushing port opening/closing part 740 detachably coupled to the flushing valve unit 720. An arrow D1 in FIGS. 1A and 1B indicates the coupling/detachment direction of the flushing port opening/closing part 740 with respect to the flushing valve unit 720.

The flushing apparatus 700, 700', 700", 700''' or 700'''' includes a replacement coupling portion 770 detachably coupled to the patient connection module 600 or 600'. The replacement coupling portion 770 is disposed in the downstream portion 713.

The flushing apparatus 700, 700', 700", 700''' or 700'''' may further include a downstream vent cap 780 detachably coupled to the replacement coupling portion 770. The downstream vent cap 780 may be coupled to the replacement coupling portion 770 so as to be interchangeable with the patient connection module 600 or 600'. An arrow C1 in FIGS. 1A and 1B shows the coupling/detachment direction of the downstream vent cap 780 with respect to the downstream portion 713 of the downstream vent cap 780.

Hereinafter, the hazardous medicinal liquid injection apparatus 1 according to one embodiment will be described with reference to FIG. 1A by focusing on the differences from another embodiment.

The port module 200 according to one embodiment is disposed on the connection pipe 300. The port module 200 includes a first extension portion 210 connected to a downstream end of a first connection portion 310. A first port 210a is formed at the end of the first extension portion 210. Through the first port 210a, a liquid in the first extension portion 210 may move into the first connection portion 310, or a liquid in the first connection portion 310 may move into the first extension portion 210. The port module 200 includes a second extension portion 220 connected to an upstream end of a second connection portion 320. A second port 220a is formed at the end of the second extension portion 220. Through the second port 220a, a liquid in the second extension portion 220 may move into the second connection portion 320.

The port module 200 includes an inlet portion 230 configured to introduce a liquid from the outside. An inlet port 230a is formed at the end of the inlet portion 230. An external liquid may move into the inlet portion 230 through the inlet port 230a.

The port module 200 may include a swabable valve 231 disposed in the inlet port 230a. The swabable valve 231 may be configured to open the inlet port 230a when the syringe tip is pressed against the inlet port 230a.

The port module 200 includes an inlet port opening/closing part 240 configured to be detachably coupled to the inlet portion 230. The inlet port opening/closing part 240 may cover the surface of the swabable valve 231 in a state in which the inlet port opening/closing part 240 is coupled to the inlet portion 230. This makes it possible to improve the hygiene of the apparatus. An arrow E1 in FIG. 1A indicates the coupling/detachment direction of the inlet port opening/closing part 240 with respect to the inlet portion 230.

The connection pipe 300 according to one embodiment includes a first connection portion 310 configured to connect the discharge port portion 111 and the first extension portion 210 of the port module 200. The connection pipe 300 includes a second connection portion 320 configured to connect the second extension portion 220 of the port module 200 and the filter module 500. The connection pipe 300 includes a third connection portion 330 configured to connect the filter module 500 and the upstream portion 711 of the flushing apparatus 700, 700', 700", 700''' or 700''''.

The connection pipe opening/closing module 400 according to one embodiment includes a first opening/closing module 410 configured to switch opening and closing of one point B1 of the first connection portion 310. The connection pipe opening/closing module 400 includes a second opening/closing module 420 configured to switch opening and closing of one point B2 of the second connection portion 320.

In one embodiment shown in FIG. 1A, the priming process, the medicinal liquid injecting process and the flushing process are described below. In the priming process according to one embodiment, the inlet port opening/closing part 240 is separated from the inlet portion 230, and a passage of the first connection portion 310 (see B1) is blocked by the first connection pipe opening/closing module 410. A passage of the remaining portion of the connection pipe 300 except for the first connection portion 310 is opened. Referring to arrows F1, F3 and F4, when the priming liquid is introduced into the inlet port 230*a* from the outside, the priming liquid flows sequentially through the inlet portion 230, the second extension portion 220, the second connection portion 330, the third connection portion 330 and the first flow path P1, whereby most of the connection pipe 300 and the inside of the first flow path P1 are filled with the priming liquid.

In the priming process, in order to remove an air remaining in the second flow path P2, the priming liquid may be introduced into the flushing valve unit 720 from the outside after additionally separating the flushing port opening/closing part 740 from the flushing valve unit 720. Referring to an arrow F5, the priming liquid flowing into the flushing valve unit 720 flows sequentially through the second flow path P2 and the downstream flow path portion P1*b*, such that the inside of the second flow path P2 is filled with the priming liquid. In this case, the air in the second flow path P2 may be discharged to the outside through the downstream portion 713.

In the priming process, in order to remove the air remaining in the second flow path P2, in a state in which the below-described flushing vent cap 730 instead of the flushing valve unit 720 is coupled to the flushing portion 715 according to the below-described fifth embodiment (see FIG. 11), a part of the priming liquid flowing into the upstream flow path portion P1*a* from the connection pipe 300 flows to the downstream flow path portion P1*b* via the upstream flow path portion P1*a* (see the arrow F4), and the remaining priming liquid flows to the second flow path P2 via the upstream flow path portion P1*a* (see the arrow F6). In this case, the air in the second flow path P2 may be discharged to the outside through the flushing vent cap 730. Thus, it is unnecessary to perform an operation of introducing the priming liquid from the outside at two or more positions in the hazardous medicinal liquid injection apparatus. This enables medical staff to more conveniently use the hazardous medicinal liquid injection apparatus.

In one embodiment, the medicinal liquid injecting process is performed after the priming process. In the medicinal liquid injecting process according to one embodiment, the inlet port opening/closing part 240 is separated from the inlet portion 230, the passage of the second connection portion 320 is blocked by the second connection pipe opening/closing module 420, and the first connection portion 310 is opened by separating the first connection pipe opening/closing module 410 from the first connection portion 310. In addition, the flushing port opening/closing part 740 is coupled to the flushing valve unit 720 to block the flushing port 715*a*. Referring to the arrow F0, when the hazardous medicinal liquid is introduced into the inlet port 230*a* from the outside, the hazardous medicinal liquid flows into the first connection portion 310 through the inlet portion 230 and the first extension portion 210. As the hazardous medicinal liquid flows into the chamber 110 from the first connection portion 310, the pressurization surface 122 moves in the direction Ap2. Thereafter, the inlet port opening/closing part 240 is coupled to the inlet portion 230 to block the inlet port 230*a*, and the second connection pipe opening/closing module 420 is separated from the second connection portion 320 to keep the connection pipe 300 in an open state. Referring to the arrows F2, F3 and F4, the pressurization surface 122 is then moved in the pressurization direction Ap1 such that the hazardous medicinal liquid is introduced into the body of a patient after sequentially passing through the connection pipe 300, the flushing apparatus 700, 700', 700", 700''' or 700'''' and the patient connection module 600 or 600'.

In one embodiment, the flushing process is performed after the medicinal liquid injecting process. In the flushing process according to one embodiment, after the flushing port opening/closing part 740 is separated from the flushing valve unit 720, the flushing liquid may be introduced into the flushing valve unit 720 from the outside. Referring to the arrow F5, the flushing liquid introduced into the flushing valve unit 720 flows sequentially through the second flow path P2, the downstream flow path portion P1*b* and the patient connection module 600 or 600', whereby the flushing liquid begins to flow into the body of a patient, what which time the flushing process is terminated.

Hereinafter, the hazardous medicinal liquid injection apparatus 1' according to another embodiment will be described with reference to FIG. 1B by focusing on the differences from one embodiment. The port module 200' according to another embodiment is disposed on the outer surface of the chamber 110. The port module 200' forms a passage that connects the outside and the internal spaces of the chamber 110. The port module 200' is configured to allow a liquid to flow into the internal space of the chamber 110 through the port module 200'.

The port module 200' includes an inlet portion 230' configured to introduce a liquid from the outside. An inlet port 230*a*' is formed at the end of the inlet portion 230'. An external liquid may move into the inlet portion 230' through the inlet port 230*a*'.

The port module 200' may include a swabable valve 231' disposed in the inlet port 230*a*'. The port module 200' includes an inlet port opening/closing part 240' detachably coupled to the inlet portion 230'. An arrow E1' in FIG. 1A indicates the coupling/detachment direction of the inlet port opening/closing part 240' with respect to the inlet portion 230'.

The connection pipe 300' according to another embodiment includes a filter upstream connection portion 315' configured to connect the discharge port portion 111 and the filter module 500. The connection pipe 300' includes a filter downstream connection portion 330 configured to connect the filter module 500 and the upstream portion 711 of the flushing apparatus.

The connection pipe opening/closing module 400' according to another embodiment may switch opening and closing of one point B1' of the filter upstream connection portion 315'.

In another embodiment shown in FIG. 1B, the priming process and the medicinal liquid injecting process are described below. The flushing process of another embodiment is the same as that of the one embodiment above. Therefore, the description thereof will be omitted. In the priming process according to another embodiment, the inlet port opening/closing part 240' is separated from the inlet portion 230', and the passage (see B1') of the filter upstream connection portion 315' is blocked by the connection pipe opening/closing module 400. Referring to the arrow F0', when the priming liquid is introduced from the outside into the inlet port 230*a*', the pressurization surface 122 moves in the opposite direction Ap2 as the priming liquid flows into the chamber 110 through the inlet portion 230'. Thereafter, the inlet port opening/closing part 240' is coupled to the inlet portion 230' to block the inlet port 230*a*', and the connection pipe opening/closing module 400 is separated from the filter upstream connecting portion 315', thereby keeping the connection pipe 300 in an open state. Referring to the arrows F2, F3 and F4, the pressurization surface 122 is then moved in the pressurization direction Ap1 such that the priming liquid flows sequentially through the discharge port portion 111, the filter upstream connection portion 315', the filter downstream connection portion 330 and the first flow path P1, whereby the interior of the connection pipe 300' and the first flow path P1 are filled with the priming liquid. In addition, the configuration/method of removing the air in the second flow path P2 in the priming process are the same as those of one embodiment. Therefore, the description thereof will be omitted.

In another embodiment, the medicinal liquid injecting process is performed after the priming process. In the medicinal liquid injecting process according to another embodiment, the inlet port opening/closing part 240' is separated from the inlet portion 230', and the passage of the filter upstream connection portion 315' is blocked by the connection pipe opening/closing module 400. Referring to the arrow F0', when the hazardous medicinal liquid is introduced into the inlet port 230a' from the outside, the pressurization surface 122 moves in the opposite direction Ap2 as the hazardous medicinal liquid flows into the chamber 110 through the inlet portion 230'. Thereafter, the inlet port opening/closing part 240' is coupled to the inlet portion 230' to block the inlet port 230a', and the connection pipe opening/closing module 400 is separated from the filter upstream connection portion 315', thereby keeping the connection pipe 300 in an open state. Referring to the arrows F2, F3 and F4, the pressurization surface 122 is then moved in the pressurization direction Ap1 such that the hazardous medicinal liquid is introduced into the body of a patient after sequentially passing through the connection pipe 300', the flushing apparatus 700, 700', 700'', 700''' or 700'''' and the patient connection module 600 or 600'.

Hereinafter, the flushing apparatus 700 according to the first embodiment of the present disclosure will be described in detail with reference to FIGS. 2 to 4.

The flushing apparatus 700 forms a predetermined flow path P therein. The flow path P includes the first flow path P1 configured to connect the upstream end of the connection pipe 300 or 300' and an upstream end of the patient connection module 600 or 600'. The first flow path may be formed in a straight line shape.

The first flow path P1 includes the upstream flow path portion P1a disposed on an upstream side and the downstream flow path portion P1b disposed on a downstream side with respect to the connection point P1F. The upstream flow path portion P1a is a portion of the first flow path P1. The downstream flow path portion P1b is a portion of the first flow path P1. The upstream flow path portion P1a connects from an upstream end of the first flow path P1 to the connection point P1F. The downstream flow path portion P1b connects from the connection point P1F to a downstream end of the first flow path P1. The upstream flow path portion P1a may be formed longer than the downstream flow path portion P1b.

The flow path P includes the second flow path P2 having one end connected to the connection point P1F of the first flow path P1. The second flow path P2 connects the connection point P1F and the flushing port 715a to be described later. The second flow path P2 may extend in a direction away from the first flow path P1.

An adjustment flow path P1a1 is formed as a portion of the first flow path P1. The upstream flow path portion P1a includes the adjustment flow path P1a1. The adjustment flow path P1a1 is formed by a flow rate reduction part 760. The adjustment flow path P1a1 performs a function of increasing a fluid resistance so as to reduce the flow rate of a liquid flowing therein. The adjustment flow path P1a1 has a relatively small cross-sectional area compared with other portions of the first flow path P1.

A connection flow path P1a2 is configured as another portion of the first flow path P1. The upstream flow path portion P1a includes the connection flow path P1a2. The connection flow path P1a2 connects from a downstream end P1E of the flow rate reduction part 760 to the connection point P1F. The downstream end P1E of the adjustment flow path P1a1 is an upstream end of the connection flow path P1a2. The connection flow path P1a2 is formed by a joint part 710A.

An inlet flow path P1a3 may be configured as a further portion of the first flow path P1. The upstream flow path portion P1a includes the inlet flow path P1a3. The inlet flow path P1a3 connects from the upstream port 711a to the upstream end of the adjustment flow path P1a1. An upstream end of the inlet flow path P1a3 forms the upstream port 711a. The inlet flow path P1a3 may be formed by the cover part 710B. Although not shown, in another example, the upstream end of the adjustment flow path P1a1 may form the upstream port 711a without a separate inlet flow path P1a3.

The main body 710 includes a joint part 710A configured to form at least the connection flow path P1a2. The joint part 710A may form the downstream flow path portion P1b. The joint part 710A may form at least a portion of the second flow path P2. The joint part 710A forms a portion of the upstream portion 711.

The joint part 710A is integrally formed. The joint part 710A is one component. For example, the joint part 710A is integrally formed by injection molding. The joint part 710A is formed so as not to be separated unless it is broken. This makes it possible to reduce the probability of occurrence of a dangerous situation in which the hazardous medicinal liquid is exposed to the outside as the user accidentally separates the joint part 710A when disposing the flushing apparatus 700 after the flushing process. In addition, if the joint part 710A is composed of assembled components, impurities may flow into the first flow path P1. Since the joint part 710A is integrally formed, it is possible to realize a more hygienic flushing apparatus 700.

The connection flow path P1a2 may be shorter than the downstream flow path portion P1b. This makes it possible to reduce the material cost of the integrally-formed joint part 710A. In addition, this makes it possible to reduce the amount of the hazardous medicinal liquid filled in the connection flow path P1a2 in the flushing process, thereby reducing the amount of the hazardous medicinal liquid which may be unnecessarily wasted in the case of attempting to inject the hazardous medicinal liquid into a patient as much as possible.

The main body 710 includes a cover part 710B coupled to the joint part 710A. A downstream side portion of the cover part 710B is inserted into the joint part 710A. One of the joint part 710A and the cover part 710B includes a coupling portion 710A1 protruding in a direction toward the other. The other of the joint part 710A and the cover part 710B includes a coupling counterpart 710B1 to which the coupling portion 710A1 is engaged. In the present embodiment, a hook-type coupling portion 710A1 is formed in the joint part 710A, and a groove-type coupling counterpart 710B1, to which the coupling portion 710A1 is engaged, is formed in the cover part 710B.

The cover part 710B accommodates the flow rate reduction part 760 therein together with the joint part 710A. The joint part 710A supports the downstream end of the flow rate reduction part 760. The joint part 710A may include a first seating portion 710A2 that forms a shoulder with which the downstream end of the flow rate reduction part 760 is engaged. The cover part 710B supports an upstream end of the flow rate reduction part 760. The cover part 710B may include a second seating portion 710B2 that forms a shoulder with which the upstream end of the flow rate reduction part 760 is engaged.

The cover part 710B forms an upstream port 711a. The cover part 710B may form an inlet flow path P1a3. The cover part 710B forms a portion of the upstream portion 711. The cover part 710B is integrally formed.

The upstream portion 711 forms an upstream side portion of the first flow path P1 with respect to the connection point P1F. The upstream portion 711 is formed by the joint part 710A and the cover part 710B. The upstream portion 711 forms an upstream port 711a through which a liquid is introduced from the connection pipe 300 or 300'.

The downstream portion 713 forms a downstream side portion of the first flow path P1 with respect to the connection point P1F. The downstream portion 713 is formed by the joint part 710A. The downstream portion 713 forms a downstream port 713a through which a liquid flows out from the first flow path P1 to the downstream side.

The downstream portion 713 includes a locking portion 713b configured to prevent the replacement coupling portion 770 from being separated from the downstream portion 713. The locking portion 713b may be formed to protrude from the outer surface of the downstream portion 713. An upstream side surface of the locking portion 713b contacts a portion of the replacement coupling portion 770 to limit the downstream side movement range of the replacement coupling portion 770.

The flushing portion 715 forms the second flow path P2. At least a portion of the flushing portion 715 is formed by the joint part 710A. The flushing portion 715 forms a flushing port 715a for introducing the flushing liquid into the second flow path P2.

The flow rate reduction part 760 is configured to reduce the flow rate of the hazardous medicinal liquid flowing through the first flow path P1. With other conditions being the same, the flow rate of a liquid flowing through the first flow path P1 is lower in the flushing apparatus 700 with the flow rate reduction part 760 than in the flushing apparatus without the flow rate reduction part 760. Although not shown, it may be possible to adopt a flow rate reduction part that enables the user to change and control the flow rate.

The flow rate reduction part 760 is disposed at an upstream side of the connection point P1F in the first flow path P1. The downstream end of the flow rate reduction part 760 is inserted into the joint part 710A. The upstream end of the flow rate reduction part 760 is inserted into the cover part 710B.

In the present embodiment, the flow rate reduction part 760 includes an adjustment flow path forming portion 761 configured to form the adjustment flow path P1a1. The flow rate reduction part 760 includes a sealing portion 762 disposed between the outer circumferential surface of the adjustment flow path forming portion 761 and the inner circumferential portion of the main body 710. The flow rate reduction part 760 may include a spacer 763 disposed at an end of the adjustment flow path forming portion 761. The flow rate reduction part 760 may include a first spacer 763a disposed between the upstream end of the adjustment flow path forming portion 761 and the second seating portion 710B2. The flow rate reduction part 760 may include a second spacer 763b disposed between a downstream end of the adjustment flow path forming portion 761 and the first seating portion 710A2. Although not shown, the flow rate reduction part 760 may further include a filter part (not shown) disposed at the upstream end of the adjustment flow path P1a1.

The replacement coupling portion 770 is disposed in the downstream portion 713. The replacement coupling portion 770 is detachably coupled to the patient connection module 600 or 600'. The replacement coupling portion 770 may be detachably coupled to the downstream vent cap 780 to be described later.

The replacement coupling portion 770 may be formed to surround an outer periphery of the downstream portion 713. An inner periphery of the replacement coupling portion 770 faces the outer periphery of the downstream portion 713.

The replacement coupling portion 770 may include a thread counterpart 771 for coupling with the patient connection module 600 or 600'. The thread counterpart 771 may be configured to engage with the downstream vent cap 780. The thread counterpart 771 may be disposed on the inner periphery of the replacement coupling portion 770.

The replacement coupling portion 770 may include a locking counterpart 772 configured to be locked to the locking portion 713b. The locking counterpart 772 may be disposed at an upstream side of the replacement coupling portion 770. The locking counterpart 772 protrudes from the inner periphery of the replacement coupling portion 770 toward the outer periphery of the downstream portion 713.

A backflow prevention part 750 prevents the flushing liquid from flowing back in a direction toward the flushing port in the second flow path P2. The backflow prevention part 750 performs a function of a check valve (one-way valve). The backflow prevention part 750 permits a flow (inflow) of a liquid moving from the second flow path P2 into the first flow path P1, but prevents a flow (outflow) of a liquid moving from the first flow path P1 into the second flow path P2.

In one example, in a state in which the flushing valve unit 720 is detached from the flushing portion 715, the backflow prevention part 750 may be configured to be coupled to and detached from the flushing portion 715. In another example, the backflow prevention part 750 may be coupled to the flushing valve unit 720 such that when the flushing valve unit 720 is detached from the flushing portion 715, the backflow prevention part 750 can be detached from the flushing portion 715 together with the flushing valve unit 720.

The backflow prevention part 750 includes a protrusion 751 protruding in an inflow direction F5. The protrusion 751 is formed of a flexible material.

A hole 751a is formed in a protruding end of the protrusion 751. The hole 751a is formed for passage of the flushing liquid. The hole 751a may be opened or closed depending on a flow direction of a liquid in the second flow path P2. The hole 751a of the protrusion 751 is opened when a liquid in the second flow path P2 flows in the inflow direction F5 (see FIG. 3). The hole 751a of the protrusion 751 is closed when a liquid does not flow in the second flow path P2 or when a liquid tries to flow in the outflow direction F6.

The backflow prevention part 750 includes a seating portion 753 seated on the flushing portion 715. The seating portion 753 may be seated at an edge portion of the flushing port 715a. The seating portion 753 supports the protrusion 751. The center of the seating portion 753 forms a hole. A liquid may move to the hole 751a of the protrusion 751 through the hole of the seating portion 753.

As an example, the protrusion 751 may be formed in a conical shape as a whole such that a vertex portion can protrude. In this case, the hole 751a is formed at the vertex portion of the protrusion 751.

Figure 6:
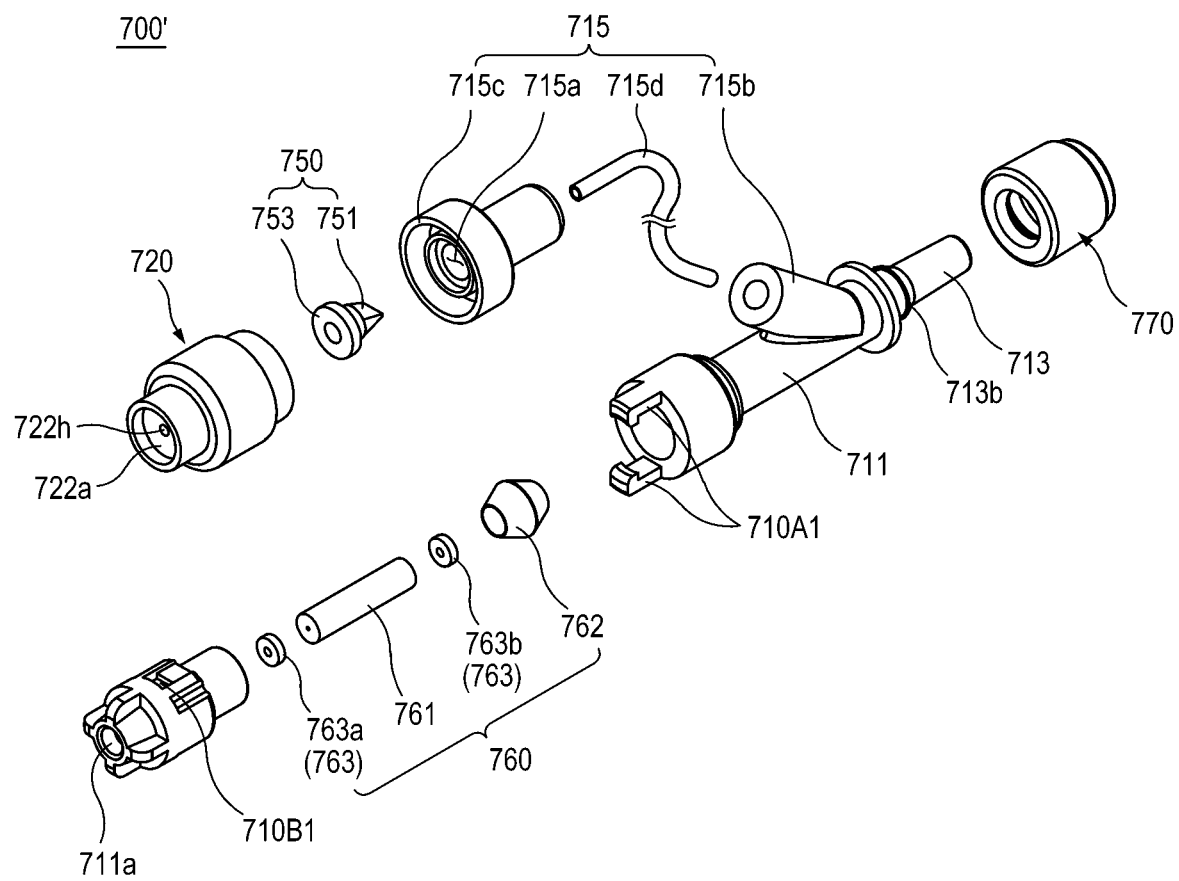
FIG. 6 is an exploded perspective view of the flushing apparatus 700' shown in FIG. 5.
Figure 9:
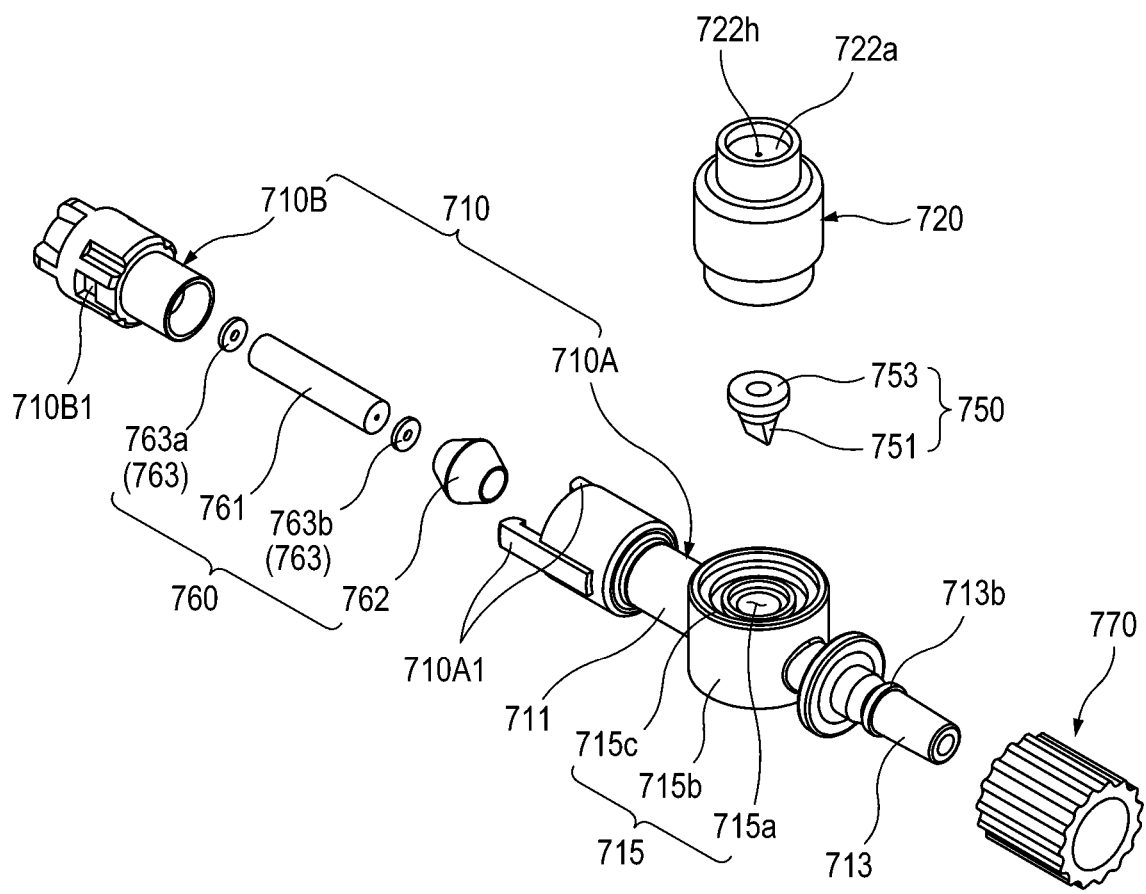
FIG. 9 is an exploded perspective view of the flushing apparatus 700" shown in FIG. 8.

In another example, the protrusion 751 may include a first inclined surface extending to incline with respect to a protruding direction thereof, a second inclined surface extending to incline in an opposite direction to the first inclined surface with respect to the protruding direction, and both side surfaces configured to cover both sides of the first inclined surface and the second inclined surface (see FIGS. 6 and 9). In this case, the first and second inclined surfaces meet at the protruding end of the protrusion 751 to form an edge, and the hole 751a is formed to extend along the edge. When a liquid in the second flow path P2 flows in the inflow direction F5, the protruding end of the first inclined surface and the protruding end of the second inclined surface are bent in opposite directions to open the hole 751a.

The flushing valve unit 720 is coupled to the flushing portion 715. The flushing valve unit 720 may be further coupled to the flushing port 715a. The flushing liquid may flow into the second flow path P2 from the outside after sequentially passing through the flushing valve unit 720 and the flushing port 715a.

The flushing valve unit 720 includes a flushing valve 722 configured to switch opening and closing of the passage of the flushing liquid. The flushing valve unit 720 includes a valve casing 721 configured to support the flushing valve 722. The flushing valve unit 720 may include a swabable valve.

Figure 3:
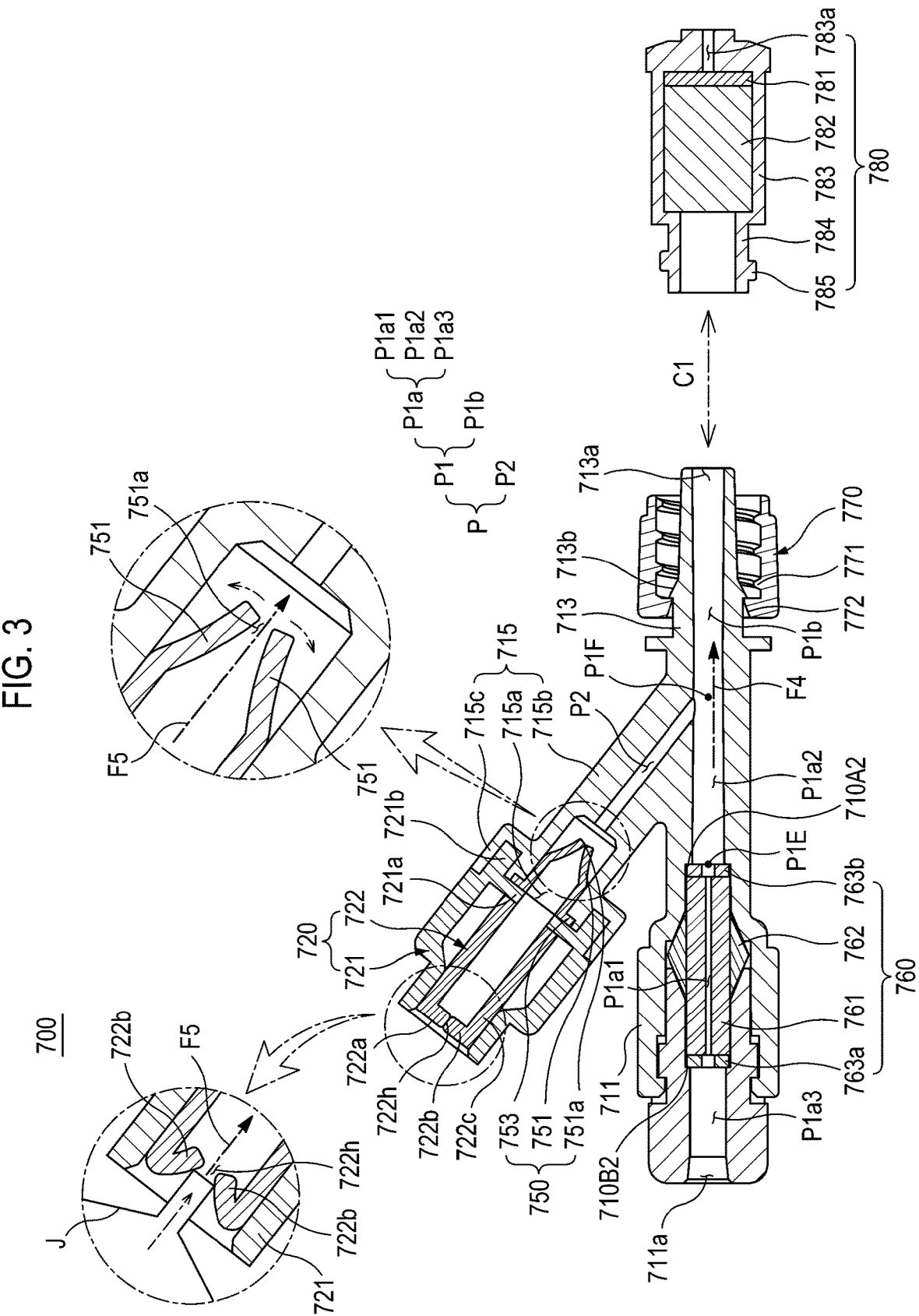
FIG. 3 is a cross-sectional view of the flushing apparatus 700 taken along a flow path P in a state in which a flushing port opening/closing part 740 is removed from FIG. 2.

The flushing valve 722 includes a surface 722a configured to form a hole 722h which is opened when the flushing valve 722 is pressed from the outside (see FIG. 3). The flushing valve 722 is formed of a flexible material. When the tip of a syringe J is pressed against the surface 722a from the outside, the surface 722a is bent to open the hole 722h.

The flushing port opening/closing part 740 opens and closes the surface 722a from the outside. The flushing port opening/closing part 740 covers the surface 722a in a state in which it is coupled to the flushing valve unit 720. The surface 722a is exposed to the outside in a state in which the flushing port opening/closing part 740 is detached from the flushing valve unit 720. With the surface 722a exposed to the outside, the user may clean the surface 722a. In some embodiments, the flushing port opening/closing part 740 may have a function of disinfecting the surface 722a in a state in which it is coupled to the flushing valve unit 720.

The flushing valve 722 includes an exposed portion 722b formed on one side to form the surface 722a. The hole 722h penetrates the exposed portion 722b. The flushing liquid introduced through the exposed portion 722b from the outside may move to the flushing port 715a.

The flushing valve 722 includes a tube portion 722c configured to support the exposed portion 722b. The tube portion 722c forms an internal space and has a tubular shape. The periphery of the exposed portion 722b is fixed to one end of the tube portion 722c, and the other end of the tube portion 722c forms a boundary of a central opening.

The valve casing 721 accommodates the flushing valve 722 therein. The valve casing 721 forms an opening at one end thereof to expose the surface 722a. The other end of the valve casing 721 is coupled to the flushing portion 715. The valve casing 721 includes a unit coupling portion 721b coupled to the flushing portion 715.

The valve casing 721 includes a pressing portion 721a configured to fix the backflow prevention part 750 in a state in which it is coupled to the flushing portion 715. The pressing portion 721a presses the seating portion 753. The seating portion 753 is sandwiched and fixed between the pressing portion 721a and the flushing portion 715.

The downstream vent cap 780 is detachably coupled to the replacement coupling portion 770 instead of the patient connection module 600 or 600'. The downstream vent cap 780 is coupled to the replacement coupling portion 770 before the start of the priming process. The downstream vent cap 780 may be detached from the replacement coupling portion 770 before the medicinal liquid injecting process. The downstream vent cap 780 is shown only in FIGS. 1A to 3. The illustration of the downstream vent cap 780 is omitted in other figures to avoid redundant descriptions.

The downstream vent cap 780 discharges a gas while blocking a discharge of the priming liquid when the priming liquid flows along the downstream portion 713 from the connection point P1F in the first flow path P1.

The downstream vent cap 780 includes a vent filter 781 which prevents passage of the priming liquid but allows passage of a gas. The vent filter 781 may include a hydrophobic filter.

The downstream vent cap 780 may include a sponge 782 disposed at an upstream side of the vent filter 781. The downstream end of the sponge 782 is in contact with the vent filter 781. The sponge 782 helps passage of a gas while absorbing the priming liquid.

The downstream vent cap 780 includes a downstream vent casing 783 configured to accommodate the vent filter 781 therein. The downstream vent casing 783 accommodates the sponge 782 therein. The downstream vent casing 783 forms a vent hole 783a through which a gas passes. The vent hole 783a is disposed at downstream side of the vent filter 781. The gas in the first flow path P1 is discharged out of the first flow path P1 after sequentially passing through the sponge 782, the vent filter 781 and the vent hole 783a.

The downstream vent cap 780 includes a downstream vent cap coupling portion 784 coupled to the replacement coupling portion 770. The downstream vent cap coupling portion 784 may be formed in a cylindrical shape. The downstream vent cap coupling portion 784 is connected to the upstream side of the downstream vent casing 783.

A thread 785 may be formed on the outer periphery of the downstream vent cap coupling portion 784. The thread 785 is formed to engage the thread counterpart 771 of the replacement coupling portion 770.

The description of the flushing apparatus 700 according to the first embodiment described above with reference to FIGS. 2 to 4 also applies to the flushing apparatus 700', 700'', 700''' or 700'''' according to the second to fifth embodiments to be described below with reference to FIGS. 5 to 11.

Figure 2:
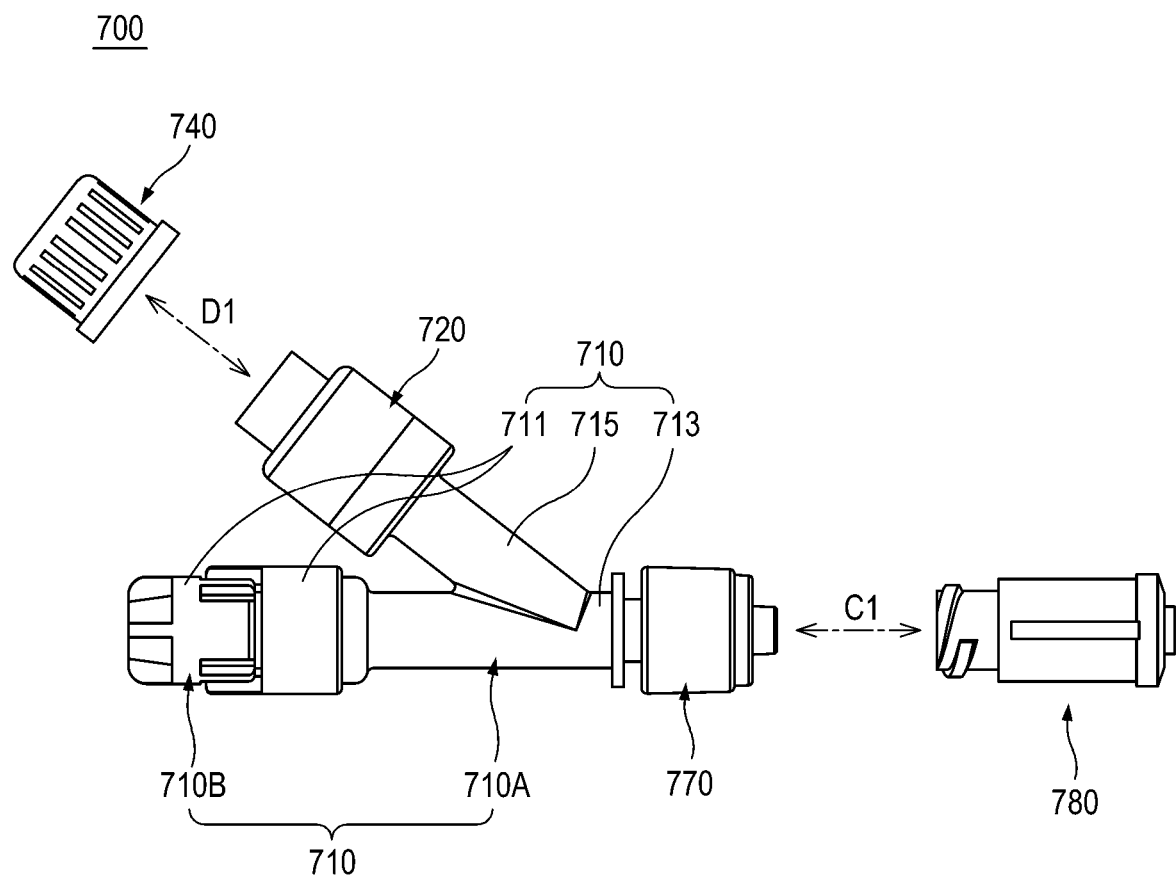
FIG. 2 is an elevation view of a flushing apparatus 700 according to a first embodiment of the hazardous medicinal liquid injection apparatuses 1 and 1' shown in FIGS. 1A and 1B.
Figure 4:
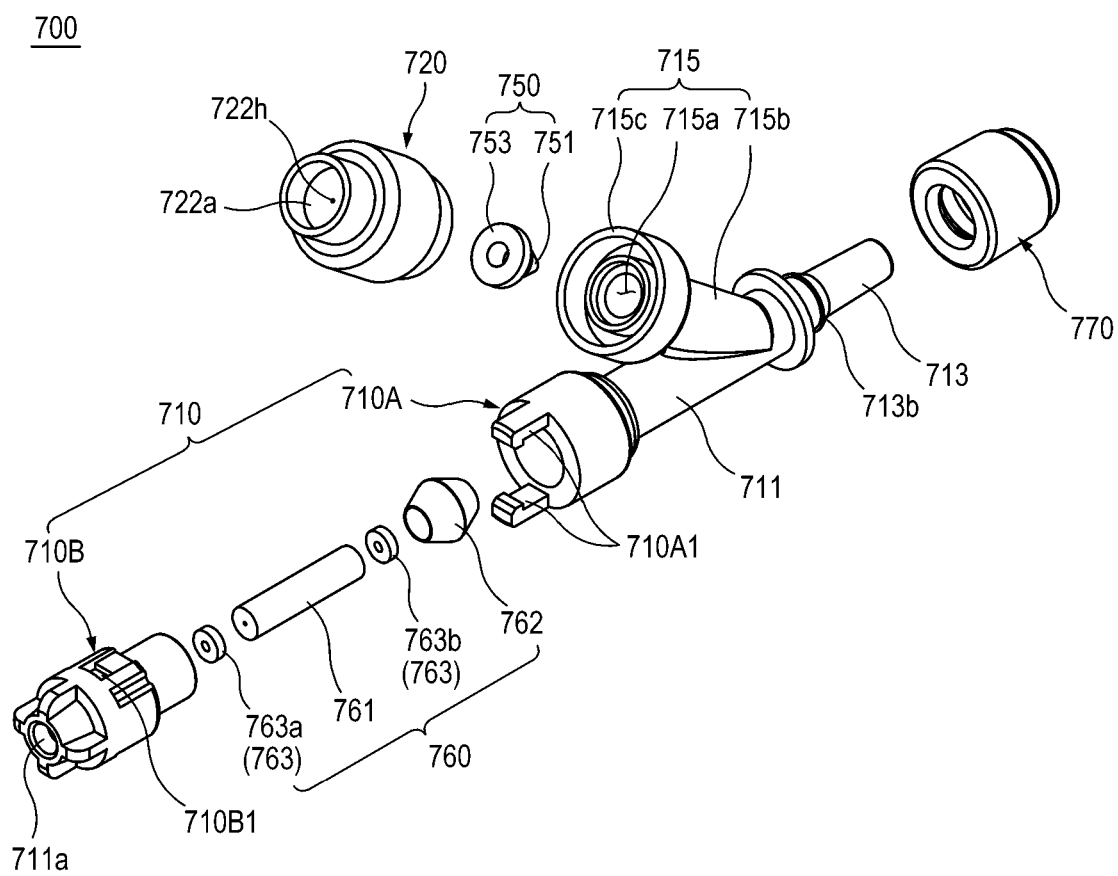
FIG. 4 is an exploded perspective view of the flushing apparatus 700 in a state in which a downstream vent cap 780 is removed from FIG. 3.

Referring to FIGS. 2 to 4, the flushing apparatus 700 according to the first embodiment includes a flushing portion 715 that forms the second flow path P2 extending, for example, at an acute angle with respect to the first flow path P1. The second flow path P2 extends from the connection point P1F in a direction between the downstream direction of the first flow path P1 and the vertical direction of the first flow path P1.

In the first embodiment, the flushing portion 715 includes a flushing joint portion 715b that forms a portion connected to the second flow path P2 and the first flow path P1. The flushing joint portion 715b is formed by the joint part 710A. The flushing portion 715 forms the flushing port 715a described above. The flushing portion 715 includes a flushing seating portion 715c to which the flushing valve unit 720 is coupled around the flushing port 715a. The unit coupling portion 721b and the flushing seating portion 715c may be coupled to each other. The backflow prevention part 750 may be disposed in the flushing port 715a.

Figure 5:
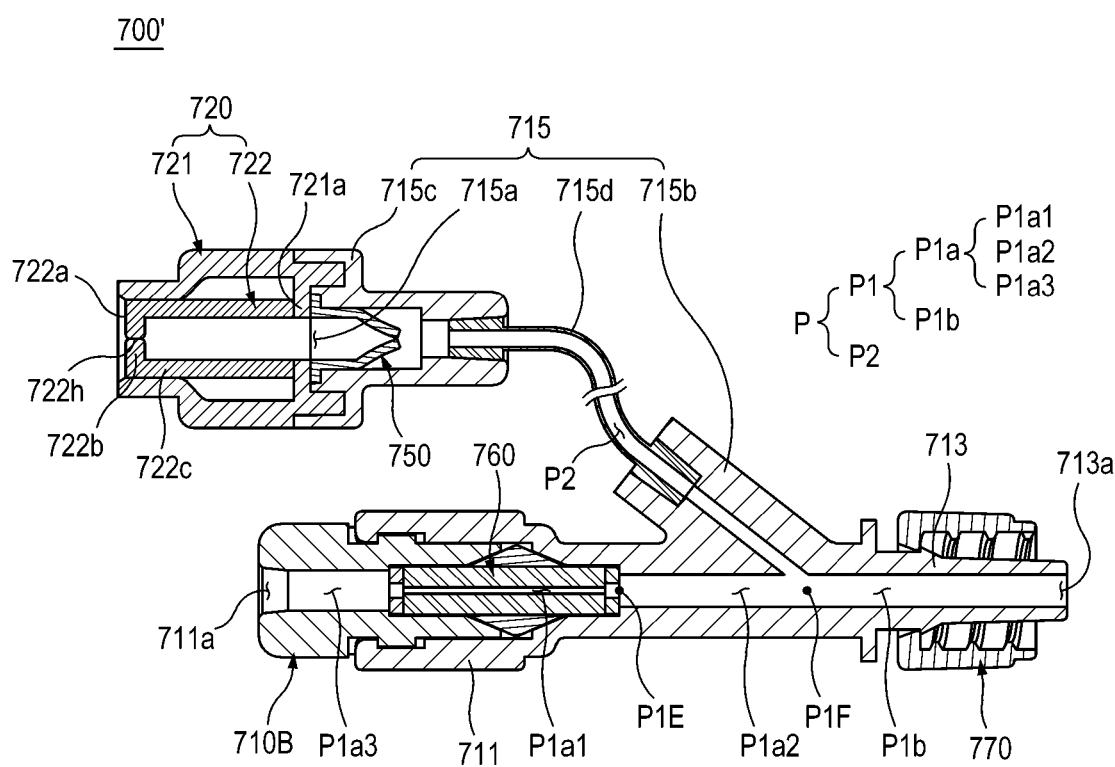
FIG. 5 is an elevation view of a flushing apparatus 700' according to a second embodiment of the hazardous medicinal liquid injection apparatuses 1 and 1' shown in FIGS. 1A and 1B.

Hereinafter, the flushing apparatus 700' according to the second embodiment will be described with reference to FIGS. 5 and 6 by focusing on the differences from the first embodiment. In the second embodiment, the flushing portion 715 further includes an extension pipe 715d made of a flexible material. The flushing portion 715 includes a flushing joint portion 715b that forms a portion of the second flow path P2 extending in a direction between the downstream direction of the first flow path P1 and the vertical direction of the first flow path P1. The extension pipe 715d connects the flushing joint portion 715b and the flushing port 715a. The extension pipe 715d forms a portion of the second flow path P2. The flushing liquid flows into the first flow path P1 from the outside after sequentially passing through the flushing port 715a, the extension pipe 715d and the flushing joint portion 715b. When the user injects the flushing liquid, the extension pipe 715d may be flexed freely according to the posture, which is convenient.

Figure 7:
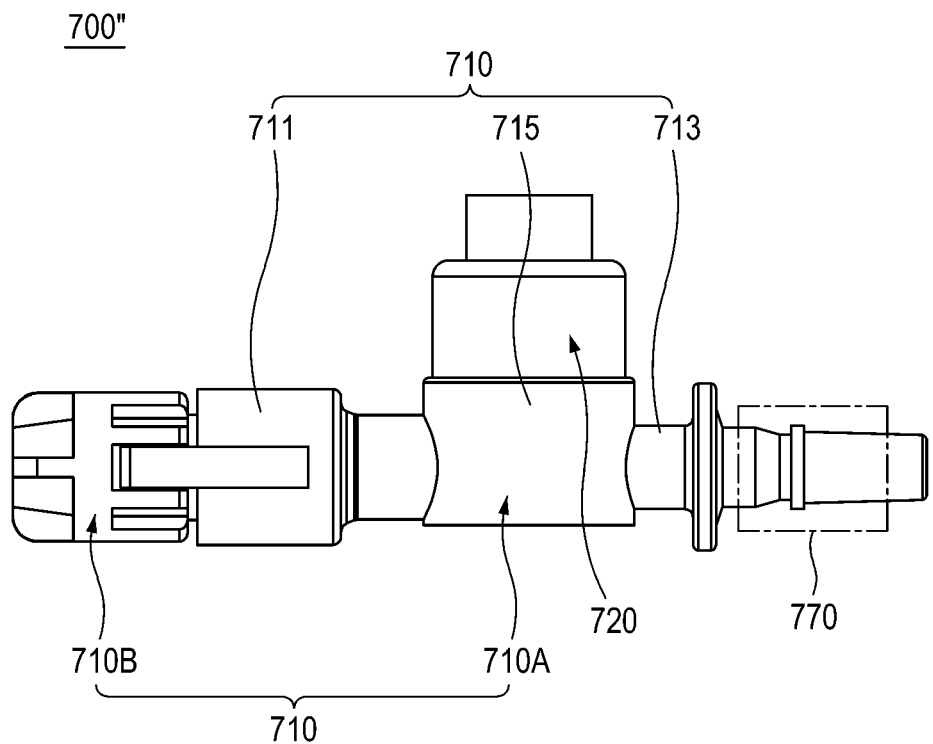
FIG. 7 is an elevation view of a flushing apparatus 700" according to a third embodiment of the hazardous medicinal liquid injection apparatuses 1 and 1' shown in FIGS. 1A and 1B.
Figure 8:
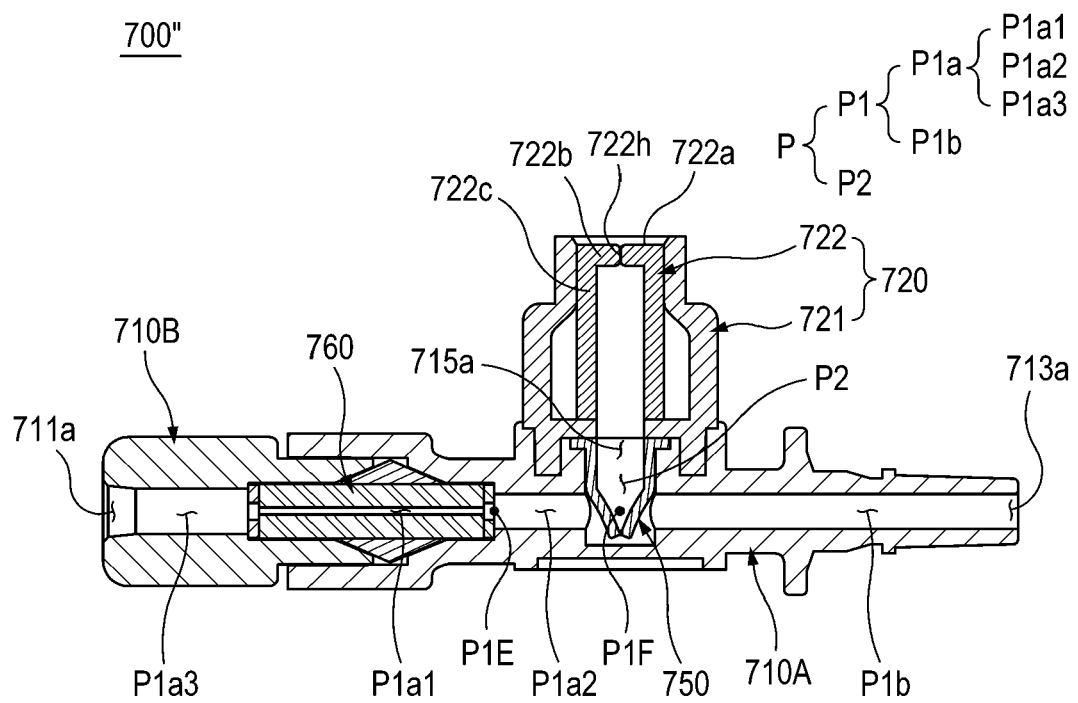
FIG. 8 is a cross-sectional view of the flushing apparatus 700" of FIG. 7 taken along a flow path P.

Hereinafter, the flushing apparatus 700" according to the third embodiment will be described with reference to FIGS. 7 to 9 by focusing on the differences from the first embodiment. The flushing apparatus 700" according to the third embodiment includes a flushing portion 715 configured to form the second flow path P2 perpendicular to the first flow path P1. The second flow path P2 may extend from the connection point P1F in the vertical direction of the first flow path P1.

In the third embodiment, at least a portion of the backflow prevention part 750 is disposed at the connection point P1F. The protrusion 751 of the backflow prevention part 750 protrudes from the second flow path P2 into the first flow path P1. The hole 751h of the protrusion 751 is disposed in the first flow path P1. In the inflow direction of the second flow path P2, the backflow prevention part 750 is disposed at a downstream end of the second flow path P2. There is no downstream side portion of the second flow path P2 with respect to the backflow prevention part 750. As a result, when the priming liquid flowing into the first flow path P1 from the connection pipe 300 or 300' fills the first flow path P1 in the priming process, it is unnecessary to separately perform an operation of removing air bubbles from the second flow path P2 in the priming process. This is convenient for medical staff. The reason is that there is no downstream portion of the second flow path P2 with respect to the backflow prevention part 750 and air is prevented by the backflow prevention part 750 from flowing into the first flow path P1 even if there is air in the upstream portion of the second flow path P2 with respect to the backflow prevention part 750.

Figure 10:
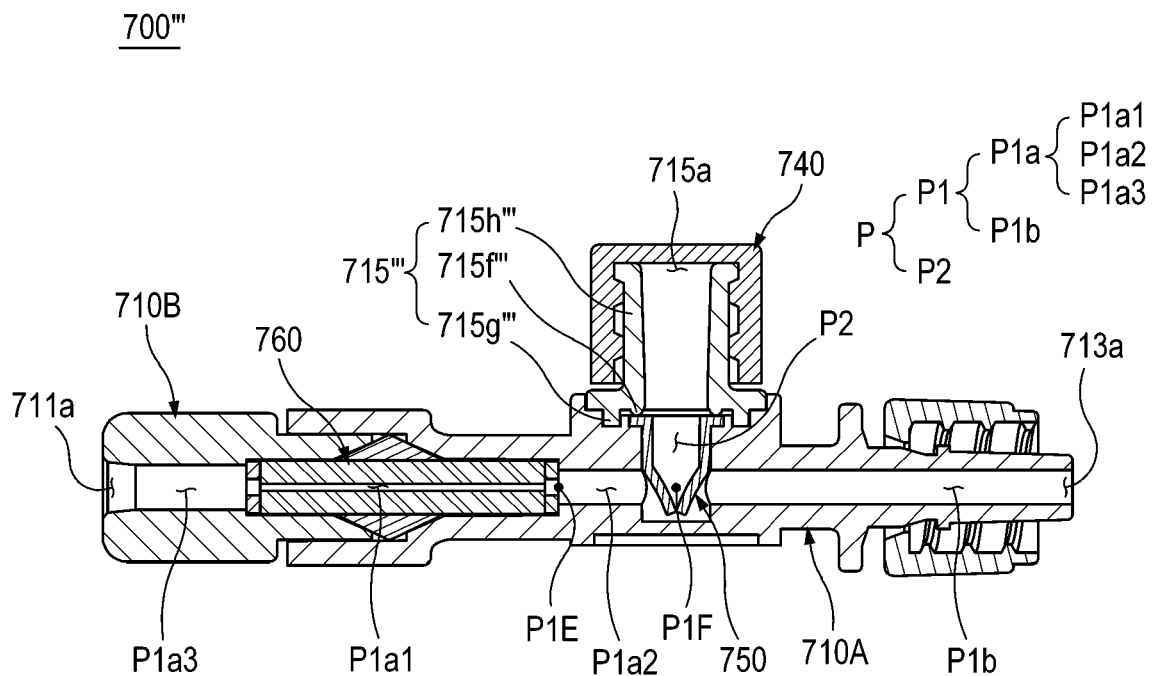
FIG. 10 is a cross-sectional view of a flushing apparatus 700''' according to a fourth embodiment of the hazardous medicinal liquid injection apparatuses 1 and 1' shown in FIGS. 1A and 1, taken along a flow path P.

The description of the flushing apparatus 700" according to the third embodiment described above with reference to FIGS. 7 to 9 also applies to the flushing apparatus 700''' according to the fourth embodiment to be described below with reference to FIG. 10.

Hereinafter, the flushing apparatus 700''' according to the fourth embodiment will be described with reference to FIG. 10 by focusing on the differences from the third embodiment. The flushing apparatus 700''' according to the fourth embodiment includes a flushing portion 715''' configured to be coupled to the flushing port opening/closing part 740 without coupling with the flushing valve unit 720. The flushing port opening/closing part 740 according to the fourth embodiment does not need to have a function for disinfecting the surface 722a. The flushing portion 715''' may include a flushing coupling portion 715g''' coupled to the joint part 710A. The flushing portion 715''' includes a pressing portion 715f''' that presses and fixes the seating portion 753 of the backflow prevention part 750. The flushing portion 715''' includes an opening/closing coupling portion 715h''' detachably coupled to the flushing port opening/closing part 740. The opening/closing coupling portion 715h''' forms a passage connected to the second flow path P2. A flushing port 715a is formed at an upstream end of the opening/closing coupling portion 715h''' based on the inflow direction of the flushing liquid. The backflow prevention part 750 is disposed at a downstream end of the flushing portion 715. The flushing port opening/closing part 740 opens or closes the flushing port 715a by being coupled to or detached from the flushing portion 715.

Figure 11:
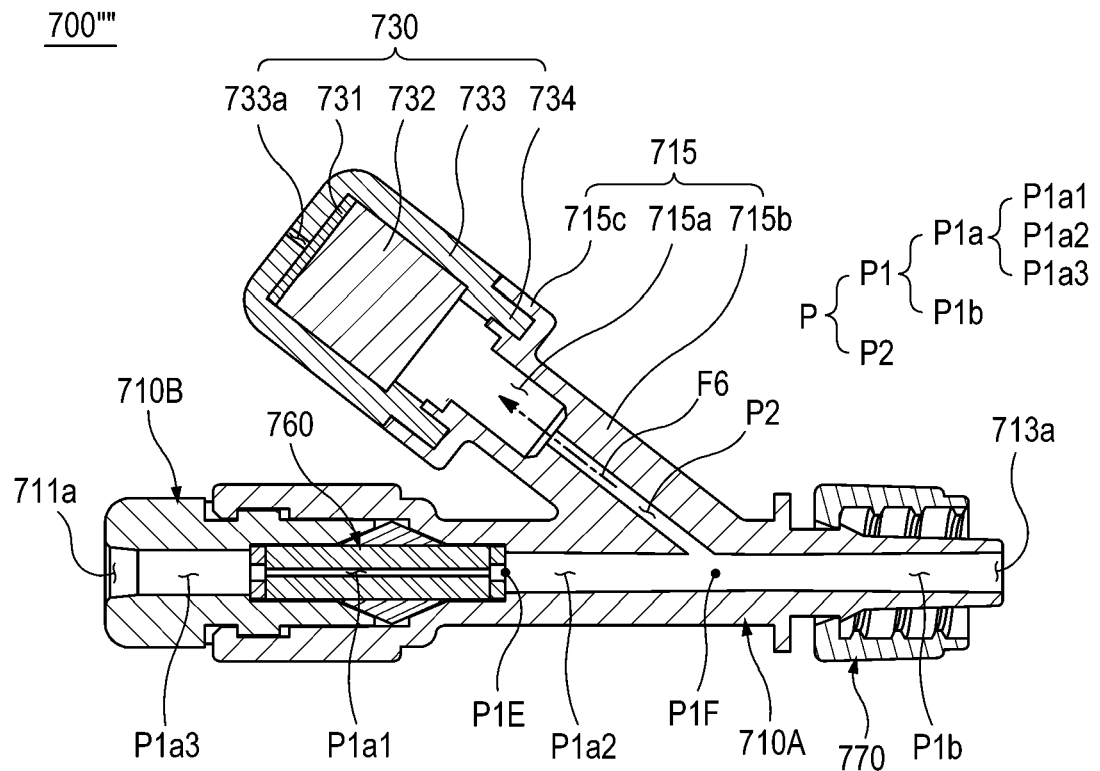
FIG. 11 is a cross-sectional view of a flushing apparatus 700'''' according to a fifth embodiment of the hazardous medicinal liquid injection apparatuses 1 and 1' shown in FIGS. 1A and 1B, taken along a flow path P.

Hereinafter, the flushing apparatus 700"" according to the fifth embodiment will be described with reference to FIG. 11 by focusing on the differences from the first embodiment. The flushing apparatus 700"" according to the fifth embodiment further includes a flushing vent cap 730 detachably coupled to the flushing portion 715. The flushing valve unit 720 may be configured to be coupled to the flushing portion 715 such that it can be replaced by the flushing vent cap 730. The flushing vent cap 730 is coupled to the flushing portion 715 before the start of the priming process. At this time, the flushing vent cap 730 is coupled to the flushing portion 715 in a state in which the flushing valve unit 720 and the backflow prevention part 750 are not coupled to the flushing portion 715. Before the medicinal liquid injecting process, the flushing vent cap 730 may be detached from the flushing portion 715, and the flushing valve unit 720 may be coupled to the flushing portion 715.

The flushing vent cap 730 discharges a gas while blocking a discharge of the priming liquid when the priming liquid flows in a direction toward the flushing port in the second flow path P2. The flushing vent cap 730 includes a vent filter 731 which prevents passage of the priming liquid but allows passage of a gas. The vent filter 731 may include a hydrophobic filter.

The downstream vent cap 780 may include a sponge 732 disposed at the upstream side of the vent filter 731. A downstream end of the sponge 732 is in contact with the vent filter 731. The sponge 732 helps passage of a gas while absorbing the priming liquid.

The downstream vent cap 780 includes a flushing vent casing 733 configured to accommodate the vent filter 731 therein. The flushing vent casing 733 accommodates the sponge 732 therein. The flushing vent casing 733 forms a vent hole 733a through which a gas passes. The vent hole 733a is disposed at downstream side of the vent filter 731. A gas in the second flow path P2 is discharged out of the second flow path P2 after sequentially passing through the sponge 732, the vent filter 731 and the vent hole 733a.

The downstream vent cap 780 includes a flushing vent cap coupling portion 734 coupled to the flushing portion 715. The flushing vent cap coupling portion 734 may be formed in a cylindrical shape. The flushing vent cap coupling portion 734 is connected to the downstream side of the flushing vent casing 733 based on the inflow direction of the flushing liquid. A thread (not shown) may be formed on the flushing vent cap coupling portion 734. The thread of the flushing vent cap 730 is formed to engage the counterpart of the flushing portion 715.

The technical idea of the present disclosure has been described heretofore with reference to some embodiments and examples shown in the accompanying drawings. However, it is to be understood that various substitutions, modifications and alterations may be made without departing from the technical idea and scope of the present disclosure that can be understood by those of ordinary skill in the technical field to which the present disclosure pertains. Further, it is to be understood that such substitutions, modifications and alterations fall within the appended claims.

What is claimed is:

1. A flushing apparatus for injection of a hazardous medicinal liquid harmful to a human body when exposed to an ambient air, comprising:
    a main body configured to connect a connection pipe for guiding the hazardous medicinal liquid and a patient connector for injecting the hazardous medicinal liquid into a patient, the main body configured to form a first flow path for guiding the hazardous medicinal liquid from the connection pipe to the patient connector, the main body including a flushing portion forming a second flow path connected to a predetermined connection point located between both ends of the first flow path and a flushing port to introduce a flushing liquid into the second flow path;
    a flow rate reducer disposed at an upstream side of the connection point in the first flow path and configured to reduce a flow rate of the hazardous medicinal liquid flowing through the first flow path;
    a flushing vent cap configured to be detachably coupled to the flushing portion and to discharge a gas while blocking a discharge of a priming liquid when the priming liquid flows in a direction toward the flushing port in the second flow path; and
    a flushing valve unit configured to be coupled to the flushing portion and to be interchangeable with the flushing vent cap, the flushing valve unit including a surface that forms a hole configured to be opened when the flushing valve unit is pressed from an outside.

2. The flushing apparatus of claim 1, wherein the main body includes an integrally-formed joint part, and
    wherein the joint part forms a connection flow path, which is a portion of the first flow path, extending from a downstream end of the flow rate reducer to the connection point.

3. The flushing apparatus of claim 2, wherein the main body includes a cover part which is coupled to the joint part and which accommodates the flow rate reducer together with the joint part.

4. The flushing apparatus of claim 2, wherein the connection flow path is shorter than a downstream flow path portion, which is a portion of the first flow path, extending from the connection point to a downstream end of the first flow path.

5. The flushing apparatus of claim 1, further comprising:
    a backflow preventer configured to prevent the flushing liquid from flowing back toward the flushing port in the second flow path.

6. The flushing apparatus of claim 5, wherein at least a portion of the backflow preventer is disposed at the connection point.

7. The flushing apparatus of claim 6, wherein the backflow preventer includes a protrusion protruding from the second flow path into the first flow path, and a hole through which the flushing liquid is passed is formed at an end of the protrusion.

8. The flushing apparatus of claim 1, wherein the main body includes a downstream portion that forms a portion of a downstream side of the connection point in the first flow path,
    wherein the flushing apparatus further includes:
    a replacement coupling portion disposed in the downstream portion and configured to be detachably coupled to the patient connector; and
    a downstream vent cap configured to be detachably coupled to the replacement coupling portion by replacing the patient connector and to discharge a gas while blocking a charge of a priming liquid when the priming liquid flows along the downstream portion from the connection point in the first flow path.

9. A hazardous medicinal liquid injection apparatus for injecting a hazardous medicinal liquid harmful to a human body when exposed to an ambient air, comprising:
    a pumping module configured to pressurize the hazardous medicinal liquid;
    a connection pipe configured such that the hazardous medicinal liquid flowing out of the pumping module by pressurization in the pumping module flows through the connection pipe; and
    a flushing apparatus configured to connect the connection pipe and a patient connector for injecting the hazardous medicinal liquid into a patient,
    wherein the flushing apparatus includes:
    a main body configured to form a first flow path for guiding the hazardous medicinal liquid from the connection pipe to the patient connector, the main body including a flushing portion forming a second flow path connected to a predetermined connection point located between both ends of the first flow path and a flushing port to introduce a flushing liquid into the second flow path;
    a flow rate reducer disposed at an upstream side of the connection point of the second flow path in the first flow path and configured to reduce a flow rate of the hazardous medicinal liquid flowing through the first flow path;
    and a flushing vent cap configured to be detachably coupled to the flushing portion and discharge a gas while blocking a discharge of a priming liquid when the priming liquid flows in a direction toward the flushing port in the second flow path; and
    a flushing valve unit configured to be coupled to the flushing portion and to be interchangeable with the flushing vent cap, the flushing valve unit including a surface that forms a hole configured to be opened when the flushing valve unit is pressed from an outside.

10. The hazardous medicinal liquid injection apparatus of claim 9, wherein the main body includes an integrally-formed joint part, and
    wherein the joint part forms a connection flow path, which is a portion of the first flow path, extending from a downstream end of the flow rate reducer to the connection point.

11. The hazardous medicinal liquid injection apparatus of claim 9, wherein the pumping module includes a chamber configured to accommodate the hazardous medicinal liquid,
    wherein the hazardous medicinal liquid injection apparatus further comprises a port module connected to the connection pipe or the chamber and configured to fill a liquid into the chamber.

* * * * *